(12) United States Patent
Hansmann et al.

(10) Patent No.: US 7,816,657 B2
(45) Date of Patent: Oct. 19, 2010

(54) PARTICLE THERAPY SYSTEM

(75) Inventors: Thomas Hansmann, Heidelberg (DE); Eike Rietzel, Darmstadt (DE)

(73) Assignee: Siemens Aktiengesellschaft, Munich (DE)

( * ) Notice: Subject to any disclaimer, the term of this patent is extended or adjusted under 35 U.S.C. 154(b) by 215 days.

(21) Appl. No.: 12/110,889

(22) Filed: Apr. 28, 2008

(65) Prior Publication Data

US 2008/0290299 A1 Nov. 27, 2008

(30) Foreign Application Priority Data

May 2, 2007 (DE) .................. 10 2007 020 599

(51) Int. Cl.
*A61N 5/10* (2006.01)
(52) U.S. Cl. .................. 250/492.3; 250/505.1
(58) Field of Classification Search .............. 250/492.3, 250/398, 505.1
See application file for complete search history.

(56) References Cited

U.S. PATENT DOCUMENTS

| | | | |
|---|---|---|---|
| 5,039,867 A * | 8/1991 | Nishihara et al. ........ | 250/492.3 |
| 6,580,084 B1 | 6/2003 | Hiramoto et al. | |
| 6,891,177 B1 * | 5/2005 | Kraft et al. ............... | 250/505.1 |
| 6,894,300 B2 * | 5/2005 | Reimoser et al. ......... | 250/505.1 |
| 7,141,810 B2 | 11/2006 | Kakiuchi et al. | |
| 2004/0069958 A1 | 4/2004 | Dahl et al. | |
| 2004/0227104 A1 * | 11/2004 | Matsuda et al. .......... | 250/492.1 |

FOREIGN PATENT DOCUMENTS

| | | |
|---|---|---|
| DE | 199 07 098 A1 | 8/2000 |
| DE | EP 1 752 992 A1 | 2/2007 |
| EP | 1 430 932 A1 | 6/2004 |
| EP | 1 477 206 A1 | 11/2004 |

OTHER PUBLICATIONS

Manabu Mizota, et al., "The High-Energy Beam-Transport System for HIMAC", Mitsubishi Electric Advance, Mitsubishi Electric Corp., Tokyo, Japan, vol. 62, Jan. 1, 1995, p. 2-04, XP000905407, ISSN:0386-5096.
European Office Action dated Nov. 7, 2008 and English translation.
European Search Report dated Oct. 30, 2008 and English translation.
German Office Action dated Apr. 21, 2008 with English translation.

* cited by examiner

*Primary Examiner*—Jack I Berman
(74) *Attorney, Agent, or Firm*—Brinks, Hofer, Gilson & Lione

(57) ABSTRACT

A particle therapy system is provided. The particle therapy system includes at least two acceleration units, with each of which acceleration units particles can be accelerated to at least an energy necessary for the irradiation; and a common energy selection system, connected downstream of the at least two acceleration units, with which system the energy of particles that have been accelerated by one of the acceleration units can be reduced.

14 Claims, 2 Drawing Sheets

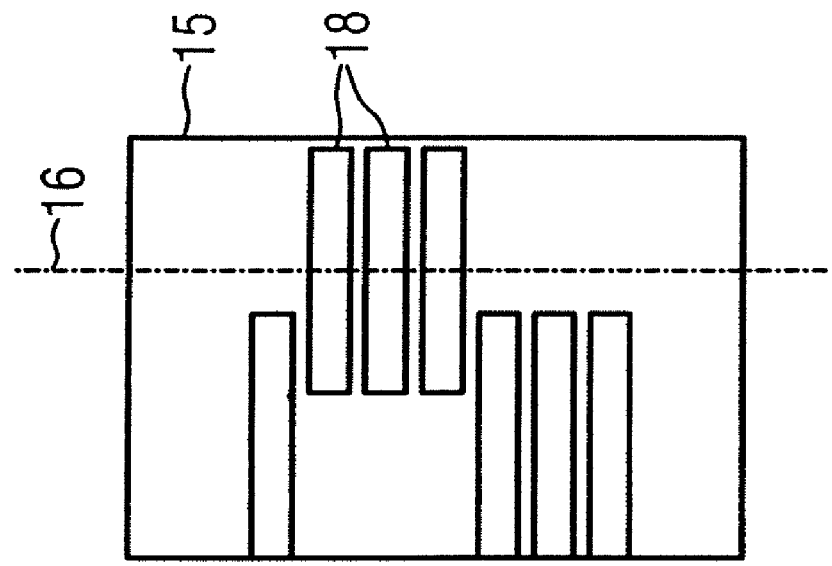
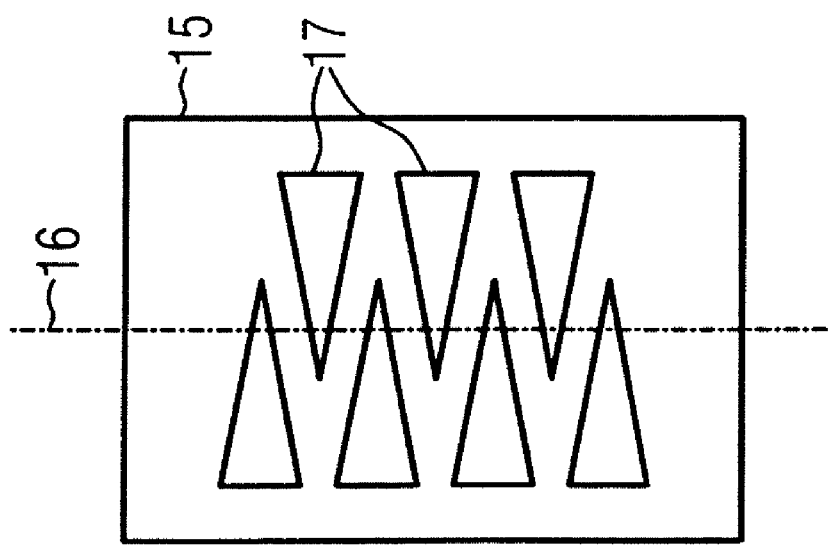

PARTICLE THERAPY SYSTEM

This patent document claims the benefit of DE 10 2007 020 599.8, filed May 2, 2007, which is hereby incorporated by reference.

BACKGROUND

The present embodiments relate to particle therapy.

Particle therapy may be used for radiation therapy. Particle therapy includes irradiating a tissue to be treated with high-energy particle radiation. Protons or carbon ions are generally used for irradiation, but other types of particles, such as pions or helium ions, may be used.

Particles interact with the tissue differently than gamma rays. As long as the particles have high energy (e.g., on the order of magnitude of >50 MeV/u), the particle interaction with the tissue is relatively low with respect to gamma rays. The interaction does not increase until after the particles have lost energy when passing through tissue. The interaction with the tissue takes place predominantly along a distance that is on the order of magnitude of a few millimeters and decreases to zero. The particle profile generated in the process is called the Bragg peak. The particle interaction makes it possible to aim the energy of the particle beam in a targeted way at a tumor, for instance, in the interior of the body while sparing the surrounding tissue and organs. The penetration depth of the particles and the site of the maximum effect are determined by the energy of the particle beam. During irradiation, energy levels for protons are generally in the range from 48 MeV/u to 250 MeV/u, and with carbon ions in the range from 85 MeV/u to 430 MeV/u.

A cyclotron is used to accelerate particles to high energy. Electrically charged particles are generated by an ion source and accelerated in the cyclotron, with strong electromagnetic fields in a spiral path, to a target energy level. The particles are expelled from the cyclotron using the fastest spiral path at the periphery of the cyclotron. After the particle beam leaves the cyclotron, the energy level is adjusted, so that the energy of the particle beam is adapted to the desired penetration depth. A selection system is connected downstream of the cyclotron. The selection system may be used to adjust the energy level. A beam transporting system is used to carry the particle beam to the desired treatment place. Further adjustment of the energy level of the particle beam—may occur downstream of the energy selection system.

Cyclotron-based particle therapy systems may accelerate two different types of particles and use the two different types of particles for irradiation. For instance, each type of particle is accelerated in its own cyclotron adapted to that type of particle.

SUMMARY AND DESCRIPTION

The present embodiments may obviate one or more of the drawbacks or limitations inherent in the related art. For example, in one embodiment, a particle therapy system includes at least two acceleration units that are constructed and operated in a simple, economical way.

In one embodiment, the particle therapy system includes at least two acceleration units. The acceleration units may accelerate particles to at least an irradiation energy level. A common energy selection system, which is connected to the acceleration units, may be used to reduce the energy of particles that have been accelerated by one of the acceleration units. The particle therapy system may be used for treatment of tumors.

One common energy selection system may be used by a plurality of acceleration units, which are parallel to one another. The beam course of the various particle beams, which emerge from the acceleration units, may be united (brought together), for example, upstream of the energy selection system. As an alternative, two parallel beam courses may be combined with a single energy selection system, for example, by positioning the energy selection system in the particular beam course where the parallel beam courses are combined.

The common energy selection system may include shielding from radiation exposure. An energy selection system may slow down the particle beams by interaction with material. Radiation exposure in the vicinity of an energy selection system is comparatively high. A single common energy selection system may include a single shielding provision from the radiation exposure. Radiation protection requirements may be reduced compared to particle therapy systems with multiple acceleration units with multiple respective downstream energy selection systems.

The at least two acceleration units may accelerate different types of particles. Each of the acceleration units may accelerate its own type of particle.

Each type of particle may include its own acceleration unit. The different types of particles generally differ in terms of mass, charge, and/or mass-charge ratio. The acceleration units may be adapted to the type of particle.

The common energy selection system may be adjoined by a beam transporting system. The beam transporting system may guide the particles to one or more treatment rooms.

In one embodiment, the acceleration units may be embodied as a cyclotron-based acceleration system. The cyclotron-based acceleration system may include a common downstream energy selection system. The particle beam emerging from a cyclotron has a fixed energy level. The particle therapy system modulates or reduces the energy of both particle beams using only a single common energy selection system. The beam transporting system may carry each particle beam from a respective cyclotron-based acceleration system to the energy selection system. The beam transporting system is adapted only to the fixed energy at which the particle beam emerges from the cyclotron. The construction with the common downstream energy selection system may, however, also be employed in other acceleration systems, such as synchrotron-based acceleration systems.

Different types of particles, such as protons or carbon ions, may be used for the acceleration and irradiation. The construction of the particle therapy system with one common energy selection system may be employed in particle therapy systems that are embodied for the joint use of protons and carbon ions.

The common energy selection system may include at least one wedgelike or platelike element.

BRIEF DESCRIPTION OF THE DRAWINGS

FIG. 2 illustrates one embodiment of an energy selection system with wedgelike beam shaping elements; and FIG. 3 illustrates an energy selection system with platelike beam shaping elements.

DETAILED DESCRIPTION

Figure 1:
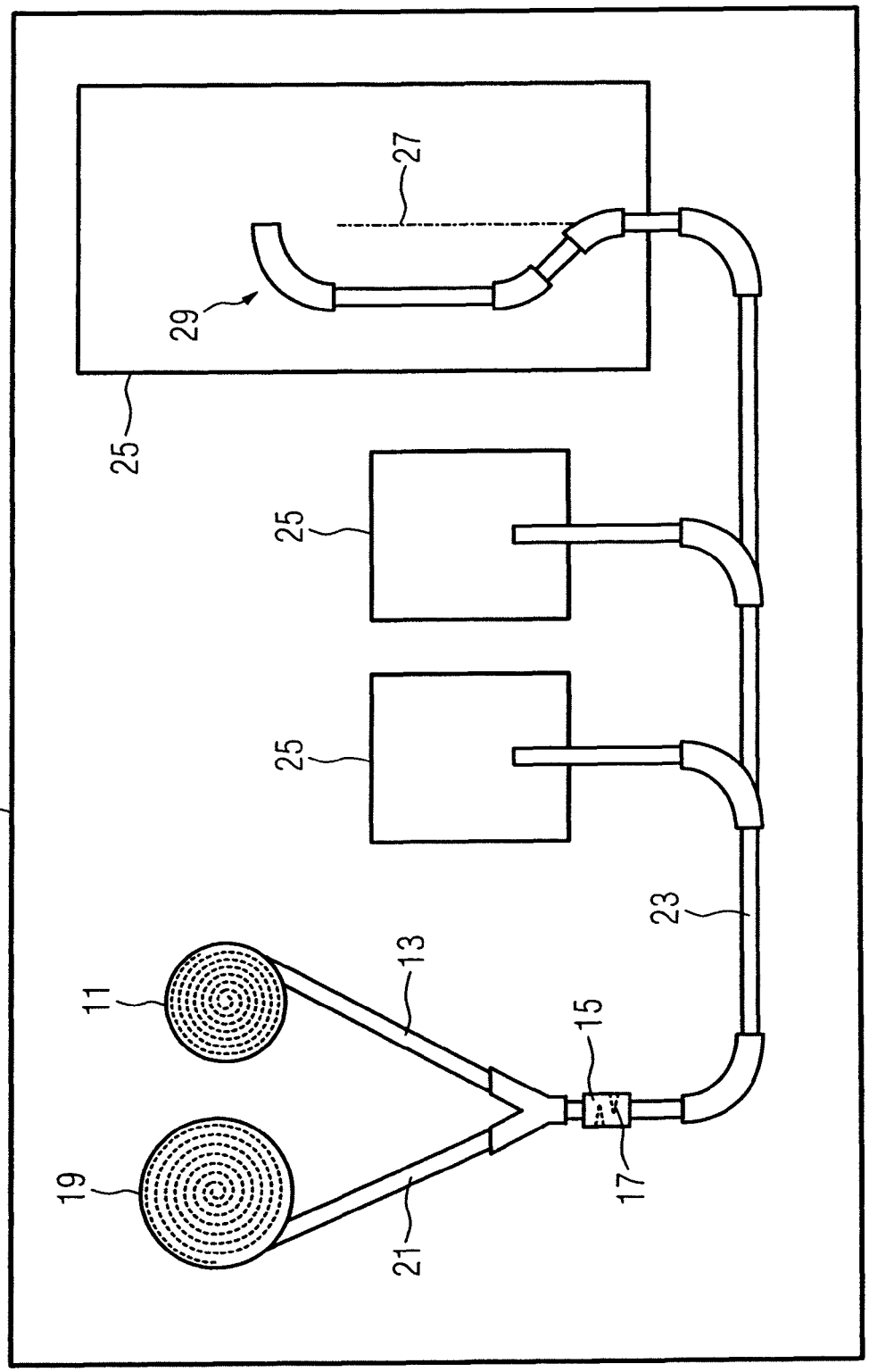
FIG. 1 illustrates one embodiment of a cyclotron-based particle therapy system.

FIG. 1 shows a particle therapy system 10. The particle therapy system 10 uses two different types of particles for the irradiation, for example, of tumors. The particles may be protons, carbon ions, pions, helium ions, or other particles.

The particle therapy system 10 may include a first cyclotron 11 and a second cyclotron 19. A first cyclotron 11 may accelerate a first type of particle to a first target energy level. The accelerated (resultant) particle beam is expelled from a first cyclotron 11 and carried, via a first beam transporting system 13 downstream of the cyclotron 11, to an energy selection system 15.

The energy selection system 15 may reduce the energy of the accelerated particle beam. For example, a first cyclotron 11 may accelerate protons to an energy of 230 MeV. The energy selection system 15 may reduce (slow down) energy of the proton beam to a variably adjustable energy level of between 230 MeV and 70 MeV.

The second cyclotron 19 may accelerate a second type of particle to a second target energy. The accelerated (resultant) particle beam is expelled from the second cyclotron 19 and carried to the same energy selection system 15 via a second beam transporting system 21 downstream of the cyclotron 19. The energy selection system 15 may set the energy of the second particle beam to a desired energy level, as described above for the first particle beam or for protons. The first cyclotron 11 and the second cyclotron 19 may be disposed side by side or arbitrarily relative to one another, for example, vertically one above the other.

Depending on which type of particle the particle therapy system is to be operated with, the generation of the particle beam may be done with the first or the second cyclotron.

The beam transporting systems 13, 21 may be disposed (inserted) between the cyclotrons 11, 19 and the energy selection system 15. The beam transporting system 13, 21 may be adapted to only one particle beam of the first type of particle with the first target energy and to a particle beam of the second type of particle with the second target energy, respectively. For example, the beam transporting system may use magnets.

In one embodiment, the particle therapy system 10 includes a beam transporting system 23. Once the particle beam has left the energy selection system 15, the downstream beam transporting system 23 carries (guides) the particle beam to the individual irradiation or treatment rooms 25. FIG. 1 shows three treatment rooms 25. In one treatment room 25, the accelerated particles are aimed at a body that is to be irradiated. The particles may be aimed at the body from a fixed direction. (e.g., in a "fixed-beam" room), or from various directions via a rotatable gantry 29 that can be moved about an axis 27.

In one embodiment, a charged particle beam is deflected by a magnet system transverse to the beam direction. In an irradiation process, which is known as raster scanning, the particle beam is scanned with a focal size of a few millimeters in layers over the target volume. Precise irradiation that conforms to the tumor is possible. For such stratified irradiation, the energy of the particle beam is finely adapted. Other irradiation processes are possible, such as spot scanning.

An irradiation process may include using passive beam shaping elements. During particle therapy, the particle beam may be flared out. A collimator and/or beam-shaping elements may be placed in the beam path, such that the particle beam is adapted to the shape of a tumor.

FIGS. 2 and 3 show embodiments of an energy selection system 15. In FIG. 2, wedgelike (wedge-shaped) beam-shaping elements 17, for example, made of carbon, are disposed into the beam path 16. In the energy selection system 15, the energy of the particle beam, which as a result of the acceleration by a cyclotron has a fixed energy, may be reduced to a desired magnitude by the wedgelike beam-shaping elements 17. The farther the wedgelike elements 17 are introduced into the beam path 16, the more the energy of the particle beam is reduced.

FIG. 3 shows another energy selection system 15. The energy selection system 15 shown in FIG. 3 functions similar to the energy selection system 15 shown in FIG. 2. In FIG. 3 the energy selection system 15 includes platelike (plate-shaped) beam-shaping elements 18. The platelike beam-shaping elements 18 may be disposed into the beam path 16. Depending on the total thickness of the platelike elements 18 through which the particle beam passes, the energy of the particle beam is reduced.

Various embodiments described herein can be used alone or in combination with one another. The forgoing detailed description has described only a few of the many possible implementations of the present invention. For this reason, this detailed description is intended by way of illustration, and not by way of limitation. It is only the following claims, including all equivalents that are intended to define the scope of this invention.

The invention claimed is:

1. A particle therapy system, comprising:
   at least two acceleration units that are operable to accelerate particles to at least an irradiation energy level; and
   a common energy selection system connected downstream of the at least two acceleration units, the common energy selection system being operable to reduce the energy of particles that have been accelerated by one of the acceleration units,
   wherein the common energy selection system connects to and is upstream of a beam transporting system that is operable to carry the particles to at least one treatment room.

2. The particle therapy system as defined by claim 1, wherein the at least two acceleration units accelerate different types of particles.

3. The particle therapy system as defined by claim 1, wherein at least one of the acceleration units is a cyclotron acceleration system.

4. The particle therapy system as defined by claim 1, wherein the common energy selection system includes at least one wedge-shaped or plate-shaped element.

5. The particle therapy system as defined by claim 1, wherein the particle types are protons, carbon ions, pions, or helium ions.

6. The particle therapy system as defined by claim 2, wherein at least one of the acceleration units is a cyclotron acceleration system.

7. The particle therapy system as defined by claim 2, wherein the common energy selection system includes at least one wedge-like or platelike element.

8. The particle therapy system as defined by claim 2, wherein at least one of the particle types is protons or carbon ions.

9. The particle therapy system as defined by claim 1, wherein the common energy selection system is operable to reduce the energy of particles that have been accelerated by the acceleration units.

10. An energy selection system, comprising:
    at least two beam transporting systems; and
    a beam-shaping element that is operable to reduce an energy level of one or more accelerated particle beams,
    wherein the at least two beam transporting systems carry at least two accelerated particle beams to the beam-shaping element, and
    wherein the energy selection system connects to and is upstream of another beam transporting system that is operable to carry the at least two accelerated particle beams to at least one treatment room.

11. The energy selection system as claimed in claim 10, wherein the at least two beam transporting systems carry the at least two accelerated particle beams from two or more cyclotrons to the beam-shaping element.

12. The energy selection system as claimed in claim 10, wherein the beam-shaping element is a wedge-shaped beam-shaping element.

13. The energy selection system as claimed in claim 10, wherein the beam-shaping element is a plate-shaped beam-shaping element.

14. The energy selection system as claimed in claim 10, comprising a plurality of beam-shaping elements.

* * * * *